United States Patent [19]

Siber et al.

[11] Patent Number: 5,412,077

[45] Date of Patent: May 2, 1995

[54] EFFECTIVE ANTIBODY TITERS AGAINST RESPIRATORY VIRUSES

[75] Inventors: George R. Siber, Brookline; Jeanne Leszczynski, Jamaica Plains, both of Mass.

[73] Assignee: Massachusetts Health Research Institute, Inc., Boston, Mass.

[21] Appl. No.: 102,106

[22] Filed: Aug. 4, 1993

Related U.S. Application Data

[63] Continuation of Ser. No. 688,435, Apr. 22, 1991, abandoned.

[51] Int. Cl.$^6$ ............... A61K 39/42; A61K 39/395; C12Q 1/70; C01N 33/569
[52] U.S. Cl. ............... 530/389.4; 435/5; 435/7.9; 435/7.92; 424/147.1
[58] Field of Search ............... 424/147.1; 530/389.4; 435/5, 32, 7.4, 7.92

[56] References Cited

U.S. PATENT DOCUMENTS

| | | | |
|---|---|---|---|
| 4,617,379 | 10/1986 | Dobkin et al. | 424/86 |
| 4,665,159 | 5/1987 | Dobkin | 424/86 |
| 4,717,766 | 1/1988 | Dobkin | 424/86 |
| 4,800,078 | 1/1989 | Prince | 424/86 |

OTHER PUBLICATIONS

Protective Activity of a Human Respiratory Syncytial Virus Immune Globulin Prepared from Donors Screened by Microneutralization Assay Jo Inf Dis 1992; 165: 456–63.
Enzyme Immunoassays for the Detection of Infections Antigens in Body Tivins: Current Limitations and Future Prospects Rev Inf Dis ; 4, #1, Jan.–Feb. 82 pp. 35–59.
Tijssen, "Practice & Theory of Enzyme Immunoassays", Elsevier, N.Y., N.Y., 1985. pp. 358–362.
Heggie, Mol Clin North Am. 67(1):17–38, 1983.
Anderson et al, J. Clin. Micro. 22(6):1050–1052, 1985.
Yolken., Rev. Infect Dis vol. 4, No. 1, Jan.–Feb. 1982 pp. 35–59.
Siber et al; Jo. Inf Dis. Mar. 1992 165(3), 456–63.
Anderson, et al., *J. Clin. Microbiol.*, vol. 22, No. 6, pp. 1050–1052 (Dec. 1985).

*Primary Examiner*—Christine M. Nucker
*Assistant Examiner*—M. P. Woodward
*Attorney, Agent, or Firm*—Elliot M. Olstein

[57] ABSTRACT

A process for identifying plasma samples containing effective antibody titers for the treatment and/or prophylaxis of infections caused by a respiratory virus. The process comprises contacting a plasma sample containing antibodies against a respiratory virus with the respiratory virus. The mixture of plasma sample and virus is then contacted with a plurality of cells. The remaining non-neutralized virus in the sample is then determined through an immunoassay following replication of the virus in the cells. Plasma samples which, at a preselected minimum antibody titer value, prevent viral replication in the cells, are then selected. Plasma from which the selected samples were derived are then pooled to provide an immunoglobulin preparation having increased effectiveness in the prophylaxis and/or treatment of infections caused by the respiratory virus.

5 Claims, No Drawings

EFFECTIVE ANTIBODY TITERS AGAINST RESPIRATORY VIRUSES

This application is a cont. of Ser. No. 07/688435, filed on Apr. 22, 1991 now abandoned.

This invention relates to the screening of plasma samples for high titers of antibodies against respiratory viruses such as respiratory syncytial virus, influenza virus, parainfluenza virus, and adenovirus. More particularly, this invention relates to the screening of plasma samples for effective amounts of antibodies against respiratory viruses through the use of neutralization assays.

In general, plasma samples taken from a plurality of individuals are screened for antibodies against a particular antigen. Those samples which have certain antibody titers against the antigen are pooled in order to make an immunoglobulin preparation for treatment of infections caused by the particular antigen or an organism or virus containing such antigen.

The screening of the plasma samples for antibodies is carried out by testing each of the plasma samples for the appropriate antibodies through the use of an appropriate assay. Suitable assays which may be employed include competitive assays, inhibition assays, immunofluorescence assays, enzyme-linked immunosorbent (ELISA) assays, sandwich assays, and neutralization assays. In determining antibody titers for each of the plasma samples, the same assay is carried out for each sample. Those samples having the desired antibody titers are then selected for the production of a pooled immunoglobulin preparation.

In accordance with an aspect of the present invention, there is provided a process for identifying, or screening, plasma samples for effective antibody titers for the treatment or prophylaxis of an infection caused by a respiratory virus. One begins the process by conducting a neutralization test or assay. The neutralization assay comprises contacting a plasma sample containing antibodies against the respiratory virus, with the respiratory virus. The resulting mixture of plasma and virus is then contacted with a population of cells. The non-neutralized virus remaining in the sample, (i.e., virus not bound by antibody and hence able to infect the cells) is then determined by means of an immunoassay after the virus which has infected the cells has been allowed to replicate for an appropriate period of time for a given respiratory virus. After the appropriate period of time, the amount of virus antigen in the cells is determined. Plasma samples which, at a preselected minimum antibody titer prevented viral replication in the cells, are then selected, and the plasma from which the selected samples were obtained is then pooled to produce an immunoglobulin.

Immunoassays which may be employed to determine the amount of virus antigen in the cells include competitive assays, inhibition assays, immunofluorescence assays, sandwich assays indirect sandwich assays, etc. Such assays are conducted according to procedures which are generally known in the art. In general, the amount of virus antigen is determined by determining the amount of a tracer which is bound, either directly or indirectly, to the virus present in the cells. The tracer includes a detectable label or marker. The marker or label may be, for example, a radioactive label, such as, for example, a radioactive isotope, a fluorescent label, such as a fluorescent dye, an absorbing dye, a chemiluminescent substance, a spin label, biotin, a chromogen, colored particles, or an enzyme label. An enzyme label is employed in an ELISA assay, whereby the amount of virus antigen present in the cells is determined by the amount of bound enzyme label present. When an ELISA assay is conducted, a suitable substrate is employed to provide color upon reaction of the substrate with the enzyme. It is to be understood, however, that the scope of the present invention is not to be limited to the specific assays and labels hereinabove described.

In a preferred embodiment, the immunoassay employed to determine the amount of virus antigen in the cells is an ELISA assay. In such an assay the cells,-upon which the neutralization portion of the process has been performed, are contacted with an antibody against the respiratory virus (or antiviral antibody) to form a virus-antibody complex. This complex is then contacted with an enzyme-linked antibody against the antiviral antibody to form a complex of virus-antiviral antibody-enzyme-linked antibody. This complex is then contacted with a substrate for the enzyme. The amount of virus in the cells is then determined. If, at a preselected minimum antibody titer, no virus is present in the cells, the plasma from which the plasma sample was obtained may be selected to become part of a pool of plasma samples which is used to prepare an immunoglobulin to be employed in the prophylaxis and treatment of a respiratory virus.

The respiratory virus may be respiratory syncytial virus, influenza virus, parainfluenza virus, or adenovirus.

The present invention, in one particularly preferred embodiment, is particularly applicable to the screening of plasma samples for effective amounts Of antibodies for the prophylaxis and/or treatment of infections caused by respiratory syncytial virus, or RSV. In one embodiment, to each well of a microtiter plate, a plasma sample from an individual is added. Then, doses of respiratory syncytial virus (Long strain) are added to each well, and the mixture of serum and virus is incubated.

After incubation a population of HEp-2 cells is added to each sample of plasma an virus and incubated for 5 days in a humidified $CO_2$ incubator. The plates are then fixed by aspirating the contents of the wells, washing the wells with phosphate-buffered saline and Tween 20, and then adding a solution of acetone-PBS. The plates are then incubated for 15 minutes, the contents then aspirated, and the plates air dried.

A serum containing antibodies against RSV, such as bovine antiRSV serum, is then added to each well.

The wells are then incubated for 1 hour and washed in phosphate-buffered saline and Tween 20, and are contacted with an enzyme-conjugated immunoglobulin against the anti-RSV antibodies. An example of such An immunoglobulin is a peroxidase-conjugated goat anti-bovine IgG. The wells are then incubated for 1 hour; and then the contents of the wells are aspirated, the wells are washed, and a substrate is added. When a peroxidase-conjugated immunoglobulin is employed, a-suitable substrate may be o-phenylenediamine dihydrochloride and hydrogen peroxide. The absorbance of each well at 492 nm is then read. Absorbance values may then be used to determine whether RSV which is in the cells is present in an amount equal to or below a predetermined level. An absorbance reading of greater than or equal to 3 standard deviations above the mean of a group of 15 control wells containing uninfected cells is considered to be evidence of virus replication. The plasma samples corresponding to those samples in which RSV which is in the cells is resent in an amount equal to or below a predetermined level may then be pooled to form an immunoglobulin preparations for the prophylaxis and/or treatment of RSV. Such an assay is further described in Anderson, et al., *J. Clin. Microbio,-* Vol. 22, No. 6, pgs. 1050-1052 (December 1985).

Applicant has found that the process of the present invention provides an accurate in vitro assay process for selecting plasma samples having an amount of antibodies effective for prophylaxis and/or treatment of a respiratory virus. Such plasma samples may then be pooled to provide an immunoglobulin preparation effective in the treatment and/or prophylaxis of a respiratory virus.

Applicant has found that by screening plasma samples for high titers of antibody against a respiratory virus through the process of the present invention, followed by the pooling of serum samples having high titers of antibody to make an immune globulin for prophylaxis or treatment of a respiratory virus, one obtains an immune globulin which provides for improved protection against or improved treatment of the respiratory virus, as compared with immune globulins prepared from serum samples screened by other assay methods. Other assay methods over which the process of the present invention is an improvement include direct ELISA's (e.g., direct ELISA's employing virally-infected cell lysate or viral proteins as antigens); competitive assays, such as, for example, those which employ an antibody (such as a monoclonal antibody) which competes with antibody contained in the test serum for binding sites of viral proteins (such competitive assays may be conducted in an ELISA format, if desired); and neutralization assays of the plaque reduction format.

The invention will now be described with respect to the following example; however, the scope of the present invention is not intended to be limited thereby.

Example 1

Microneutralization Assay

For this example, a standard high-titered IgG preparation was made in pilot experiments from the five highest-titered plasma units out of 100 units evaluated by the microneutralization assay of Anderson, et al. These five plasma samples were pooled, and a 1% IgG preparation was made from the pooled samples. This IgG preparation was then tested at various dilutions for antibody titer against RSV. The end-point titer o this standard IgG preparation is the highest dilution of the, standard preparation which gave complete inhibition of virus replication. Viral replication is defined as the optical density that is greater than or equal to 3 standard deviations above the background optical density of uninfected cells. The endpoint titer of this IgG preparation was determined to be 1:6,.000. The standard IgG preparation was therefore assigned an antibody concentration of 6,000 microneutralization units.

The following plasma samples were employed in the microneutralization assay hereinafter described:

1. A high-titered IgG(1%) preparation as hereinabove described was selected as a standard. This preparation was subjected to dilutions of 1/1,000, 1/2,000, 1/4,000, 1/6,000, and 1/8,000, which contained 6, 3, 1.5, and 0.75 microneutralization units ml of RSV antibody respectively. The diluted samples were subjected to the microneutralization assay of Anderson, et al., and a standard curve of optical densities corresponding to microneutralization units/ml was obtained. The highest dilution at which the standard prevented viral replication was typically at 1/6,000 (1 microneutralization unit/ml).

2. Control plasma samples of
   (a) Sandoz 069 intravenous immunoglobulin (IgG) at 1%, containing approximately 1,000 microneutralization units/ml;
   (b) a 1% solution of the first clinical lot of RSV intravenous immunoglobulin (Positive control ), containing approximately 2,000 microneutralization units/ml;
   (c) a virus control, which gives the maximum optical density that is observed when viral growth is not inhibited; and
   (d) a cell control, which gives the optical density expected when virus growth is completely inhibited by virus neutralizing antibodies.

Controls (a) and (b) are subjected to dilutions of 1/2,000.

3. 23 Unknown plasma samples, each subjected o a dilution of 1/2,000.

Before the dilution of the plasma samples, each sample is heat inactivated at 56° C. for 30 minutes. Each sample is then diluted as hereinabove described in minimal essential medium MEM) with 2% Fetal Calf Serum 1glutamine and 1% antibiotics added. 75 μl of each sample is added in triplicate to a well of a 96-well microtiter plate. 25 μl of respiratory syncytial virus (Long Strain) diluted in minimal essential medium to give about 100 $TCID_{50}$, is added to all wells except the cell control wells. The plate is then incubated at room temperature for 2 hours.

After the incubation, 100 ul of a suspension of HEp-2 cells ($2 \times 10^6$ cells/ml) is added to each well. The plate is then wrapped in Saran Wrap® and incubated in a-5% $CO_2$ incubator at 37° C. for 5 days. The plate is then washed three times with phosphate-buffered saline (PBS) and Tween 20, and 75 ul of 80% acetone/20% PBS is added to each well. The plate is then incubated at 4° C. for 15 minutes, and each well is then aspirated. The plate is then air dried for about 30 minutes.

The samples in each well are then subjected to an ELISA assay. 75 ul of bovine anti-RSV serum diluted (Wellcome Diagnostics, Research Triangle Park, NC) 1:1,000 in PBS/0.5% gelatin/0.15% Tween 20 with 2% normal goat serum is added to each well. The plate is then incubated for 1 hour at 37° C. in a moist chamber, and then washed four times in PBS and Tween 20. 75 ul of peroxidase-conjugated goat antibovine IgG (Kirkegaard & Perry Laboratories, Inc., Gaithersburg, Md.) diluted 1/10,000 in PBS/O 5% gelatin/0.15% Tween 20 with 2% normal goat serum is then added to each well, and the plate is incubated for 1 hour at 37° C. in a moist chamber. Each well is then washed sixtimes in PBS/Tween 20, and 125 ul of a solution of a crystalline 3,3', 5,5'-tetramethylbenzidine (TMB) substrate was added to each well. The plate is then incubated at room temperature for approximately 15 minutes. The absorbance of each well at 450 nm is then measured and the mean absorbance of each triplicate sample is calculated, to determine the amount of anti-RSV antibody in each plasma sample, from which virus antigen in the cells, and then antibody titer of the plasma sample is determined.

Screening Procedure

If a plasma sample is found to have an antibody titer against RSV of at least 1:3,000, (i.e., a 1/2000 dilution of the sample has an O.D. equal to or less than 1.5 microneutralization units in the standard IgG curve), further plasma is collected from the corresponding donor. Each time the donor donates, the plasma is tested by the microneutralization assay procedure hereinabove described to determine if the donor continues to have an RSV antibody titer of at least 1:3,000. If the donor's titer falls below 1:3,000, further plasma samples will not be collected.

Plasma samples having an RSV antibody titer of at least 1:3,000 are then checked to be Sure that such samples come from acceptable donors, and the samples are then pooled into pools containing from about 150 to about 1,200 liters. The pooled plasma may then be fractionated by conventional means to provide an immune serum globulin.

It is to be understood, however, that the scope of the present invention is not to be limited to the specific embodiments described above. The invention may be practiced other than as particularly described and still be within the scope of the accompanying claims.

What is claimed is:

1. A process for preparing an immunogloublin containing effective antibody titers for the treatment or prophylaxis of an infection caused by respiratory syncytial virus, comprising:
    recovering from plasma an immunoglobulin containing effective antibody titers for the treatment or prophylaxis of an infection caused by respiratory syncytial virus, said plasma having been selected by:
    contacting a sample of plasma containing antibodies against respiratory syncytial virus with respiratory syncytial virus;
    contacting the mixture of sample and respiratory syncytial virus with a population of cells;
    incubating the mixture for a prescribed period of time to allow non-neutralized respiratory syncytial virus remaining in the mixture to replicate in cells;
    determining the amount of respiratory syncytial virus antigen in cells by an immunoassay; and
    selecting a plasma whose sample which, at a preselected minimum antibody titer, prevents viral replication within said cells.

2. The process of claim 1 wherein said determining of the amount of said respiratory syncytial virus antigen in said cells comprises:
    contacting said sample with antibody against said respiratory syncytial virus;
    contacting said sample with an enzyme-linked antibody against said antibody against said respiratory syncytial virus;
    contacting said sample with a substrate for said enzyme; and
    determining the amount of said respiratory syncytial virus remaining in said sample by determining the amount of enzyme reacted with said substrate.

3. The process of claim 2 wherein said enzyme is a peroxidase.

4. The process of claim 3 wherein said substrate for said peroxidase is 3,3',5,5'-tetramethylbenzidine.

5. The process of claim 3 wherein said substrate for said peroxidase is o-phenylenediamine dihydrochloride and hydrogen peroxide.

* * * * *